United States Patent [19]
Scharlack

[11] Patent Number: 5,885,212
[45] Date of Patent: Mar. 23, 1999

[54] NON-INVASIVE MEASUREMENT OF BLOOD PH

[75] Inventor: Ronald S. Scharlack, Brookline, Mass.

[73] Assignee: Chiron Diagnostics Corporation, E. Walpole, Mass.

[21] Appl. No.: 871,270

[22] Filed: Jun. 9, 1997

Related U.S. Application Data

[60] Provisional application No. 60/020,082 Jun. 13, 1996.
[51] Int. Cl.$^6$ ....................................................... A61B 5/00
[52] U.S. Cl. ............................................. 600/322; 356/39
[58] Field of Search ..................................... 600/310, 311, 600/320, 322, 323, 326, 328, 473, 476; 356/39

[56] References Cited

U.S. PATENT DOCUMENTS

| | | | |
|---|---|---|---|
| 5,355,880 | 10/1994 | Thomas et al. | 128/633 |
| 5,435,309 | 7/1995 | Thomas et al. | 128/633 |

FOREIGN PATENT DOCUMENTS

| | | |
|---|---|---|
| 0586025 | 3/1994 | European Pat. Off. . |
| 0695937 | 2/1996 | European Pat. Off. . |

OTHER PUBLICATIONS

Brunzel, U. et al. "pH–Dependent Absorption in the B and Q Bands of Oxyhemoblobin and Chemically Modified Oxyhemoglobin (BME) at Low CL Concentrations" *Biophysical Journal*, vol. 49, (1986) 1069–1076.

Wimberley P., et al. "Effect of pH on the Absorption Spectrum of Human Oxyhemoglobin: a Potential Source of Error in Measuring the Oxygen Saturation of Hemoglobin" *Clinical Chemistry,* vol. 34, No. 4 (1988) 750–754.

Alam, M.K. et al., "Near–infrared spectroscopy of lysed blood: pH effects", Proceedings *SPIE,* vol. 2680, Ultrasensitive biomedical diagnostics, San Jose, CA, (1996) pp. 146–155.

Haaland et al., "Partial Least–Squares Methods for Spectral Analyses. 1. Relation to Other Quantitative Calibration Methods and the Extraction of Qualitative Information", Anal. Chem., 60 (1988) pp. 1193–1202.

Owen, "Quantitative UV–Visible Analysis in the Presence of Scattering", Hewlett–Packard Application Note, publication 12–5963–3937E, 1995, pp. 0–7.

*Primary Examiner*—Max Hindenburg
*Assistant Examiner*—Eric F. Winaker
*Attorney, Agent, or Firm*—Arthur S. Morgenstern; Charles L. Gagnebin, III

[57] ABSTRACT

Methods and apparatus are provided for non-invasively determining blood pH by a multivariate analysis technique, such as classical least squares (CLS), partial least squares (PLS), or principal components regression (PCR). The technique employs at least one spectral factor based on the difference in the spectrum of a hemoglobin fraction (e.g., oxyhemoglobin) at two different pH's (e.g., pH 7.2 and pH 7.8). The spectral factor is preferably evaluated over the wavelength range of 520–680 nm.

8 Claims, 3 Drawing Sheets

NON-INVASIVE MEASUREMENT OF BLOOD PH

This application claims the benefit of U.S. Provisional Application No.: APPLICATION NO.: 60/020,082 FILING DATE Jun. 13, 1996.

FIELD OF THE INVENTION

This invention relates to the measurement of pH and, more particularly, to the non-invasive measurement of blood pH.

BACKGROUND OF THE INVENTION

Measurement of blood pH is important in the critical care environment. Commercially available blood gas instruments measure pH, $PO_2$ and $pCO_2$. These instruments require either the extraction of a blood sample for in vitro instruments or the use of an invasive sensor for in vivo measurements. A non-invasive measurement of blood pH is desirable because it would eliminate the necessity of sample extraction or an invasive sensor, and would allow for continuous monitoring.

Hemoglobin oxygen saturation has been non-invasively monitored by means of pulse oximetry. Although widely used in the United States and elsewhere, these instruments have been limited to measuring oxygen saturation and have not provided information regarding blood pH.

U.S. Pat. No. 5,355,880 (the "'880 patent"), assigned to Sandia Corporation, presents a generalized discussion of the non-invasive (optical) measurement of blood gas parameters, including pH. Significantly, with regard to the present invention, this patent teaches away from using wavelengths in the 520–680 nm range. Thus, although the patent broadly discloses the use of wavelengths in the 500 nm to 2500 nm range to measure pH, $PCO_2$, $[HCO_3^-]$, $PO_2$, and $O_2$ saturation, in its examples it uses wavelengths in the 640–970 nm range for its multiple linear regression and best ratio analyses ('880 patent at column 24, lines 18–20 and 48–51), and in the 700–800 nm range for its partial least squares analysis ('880 patent at column 25, line 28). Further, in FIG. 10, the patent presents correlation coefficients for pH only for wavelengths in the 650–975 nm range. Along these same lines, the patent describes the prior art spectroscopic determination of pH in non-biological systems as using wavelengths in the 1100–2500 nm range ('880 patent at column 7, lines 40–42; see also column 28, lines 28–41).

The effect of pH on the spectrum of methemoglobin (MetHb) is known and has been reported in the literature. See Brunzel et al., "pH-Dependent Absorption in the B and Q Bands of Oxyhemoglobin and Chemically Modified Oxyhemoglobin (BME) at Low CL$^-$ Concentrations," *Biophysical Journal*, 49:1069–1076, 1986. The use of the MetHb spectrum for prediction of pH, however, is problematic since MetHb typically represent only about 1% of the total hemoglobin in blood.

The effect of pH on the spectrum of oxyhemoglobin ($O_2Hb$) has also been studied. See Brunzel et al., supra; and Wimberley et al., "Effect of pH on the Absorption Spectrum of Human Oxyhemoglobin: a Potential Source of Error in Measuring the Oxygen Saturation of Hemoglobin," *Clinical Chemistry*, 34:750–754, 1988. The focus of these studies, however, has not been on the use of an oxyhemoglobin spectrum to determine pH, but rather on obtaining a theoretical understanding of the chemistry of the heme group in the case of the Brunzel et al. work, and on controlling the effects of pH during the calibration of oxygen saturation meters in the case of the Wimberley et al. work. Neither reference in any way discloses or suggests the use of an oxyhemoglobin spectrum to non-invasively determine blood pH.

SUMMARY OF THE INVENTION

In view of the foregoing, it is an object of this invention to provide improved methods and apparatus for non-invasively determining blood pH. More particularly, it is an object of the invention to identify spectral factors and wavelength ranges which can be employed in such determinations, where the term "spectral factor" is used in the sense of a vector component of a calibration matrix of a multivariate analysis procedure, e.g., a procedure employing classical least squares (CLS), partial least squares (PLS), principal components regression (PCR), or the like. See, for example, Haaland et al., "Partial Least-Squares Methods for Spectral Analyses. 1. Relation to Other Quantitative Calibration Methods and the Extraction of Qualitative Information", *Anal. Chem.*, 60:1193–1202, 1988.

In accordance with the invention, it has been determined that the difference in absorbance of oxyhemoglobin at two pH's, e.g., pH 7.2 and pH 7.8, can be used as such a spectral factor. It has been further determined that a preferred wavelength range for the evaluation of this factor is between about 520 nm and about 680 nm. Wavelengths outside of this preferred range can be included in the spectral factor, e.g., wavelengths as small as about 450 nm to wavelengths as large as about 900 nm, provided that wavelengths in the 520–680 nm range are included in the factor.

As an alternative to oxyhemoglobin, the difference in absorbance of carboxyhemoglobin (COHb) at two pH's can also be used as a spectral factor, alone or in combination with the oxyhemoglobin factor. Again, the preferred wavelength range for the evaluation of this spectral factor is between about 520 nm and about 680 nm, with wavelengths outside of this range being optionally included in the factor, e.g., wavelengths as small as about 450 nm to wavelengths as large as about 900 nm.

Other spectral factors based on the variation with pH of the absorbance spectrum of methemoglobin (MetHb) and/or deoxyhemoglobin (HHb) can be used alone or in combination with the oxyhemoglobin and/or carboxyhemoglobin factors. In general, which spectral factors are used to determine pH will depend on the relative concentrations of the various hemoglobin fractions in the blood whose pH is to be determined, e.g., in the patient's arterial blood. As discussed below, in accordance with the invention, procedures are provided for combining spectral factors for the various hemoglobin fractions.

By means of these spectral factors and wavelength ranges, non-invasive measurement of blood pH can be performed using apparatus and methods of the type described in the above-referenced U.S. Pat. No. 5,355,880, the relevant portions of which are incorporated herein by reference. For example, the invention can be used to measure arterial blood pH non-invasively by utilizing the pulsatile nature of blood flow to address such patient variables as skin, fat, bone, and muscle absorption, as is done in the measurement of oxygen saturation by pulse oximetry. pH determination by this approach is a particularly preferred embodiment of the invention.

BRIEF DESCRIPTION OF THE DRAWINGS

FIG. 1B is a plot of absorbance versus wavelength for:

Curve 1: $O_2Hb_{pH\ 7.2}$

Curve 2: $O_2Hb_{pH\ 7.2} - O_2Hb_{pH\ 7.8}$

Curve 3: $O_2Hb_{pH\ 7.2} - O_2Hb_{pH\ 7.5}$

Curve 4: $O_2Hb_{pH\ 7.5} - O_2Hb_{pH\ 7.8}$

Note that curve 1 was multiplied by 0.01 before being plot in this figure.

Figure 2A:
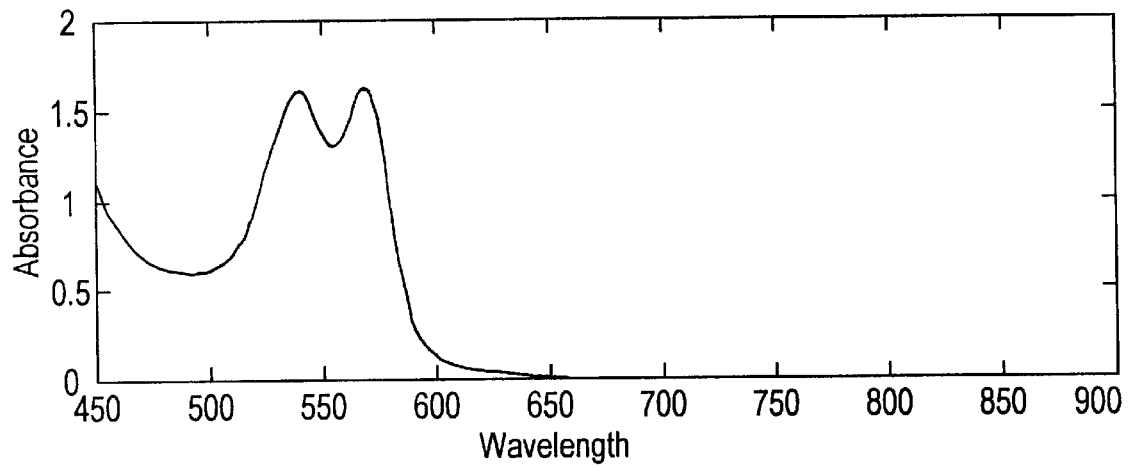

FIG. 2A is a plot of absorbance versus wavelength for $COHb_{pH\ 7.2}$.

Figure 2B:
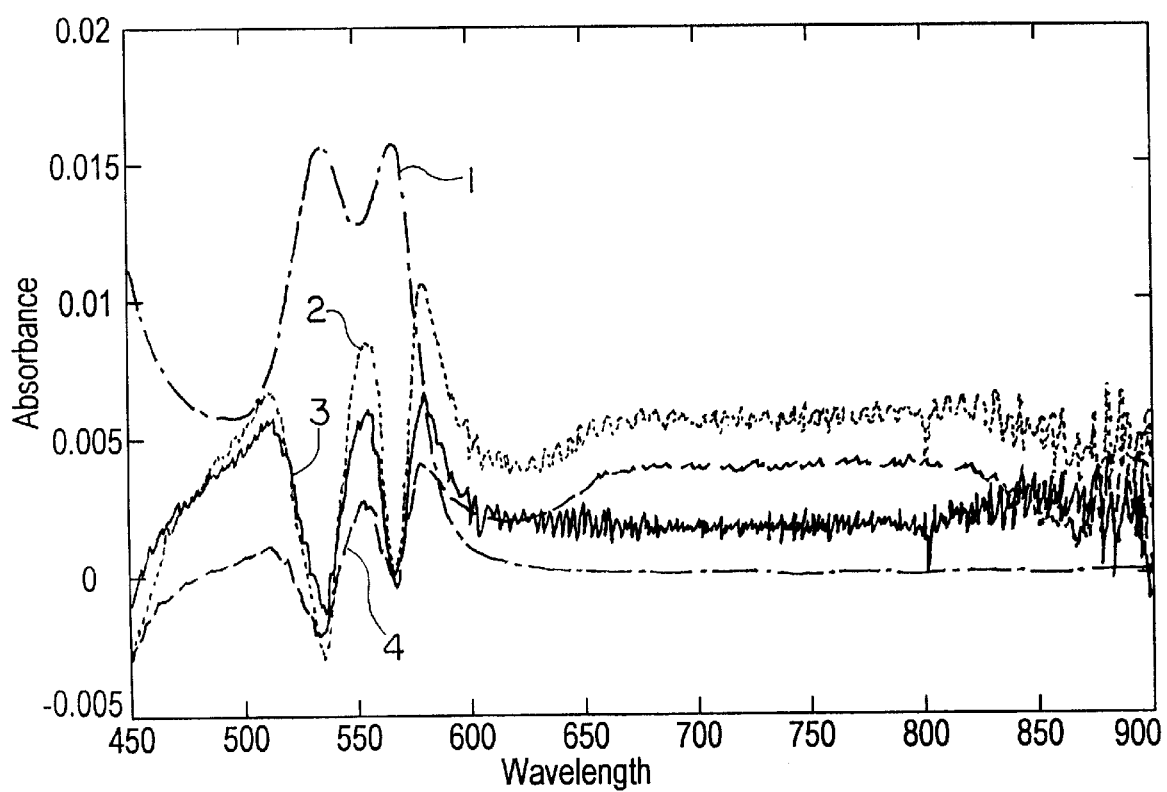

FIG. 2B is a plot of absorbance versus wavelength for:

Curve 1: $COHb_{pH\ 7.2}$

Curve 2: $COHb_{pH\ 7.2} - COHb_{pH\ 7.8}$

Curve 3: $COHb_{pH\ 7.2} - COHb_{pH\ 7.4}$

Curve 4: $COHb_{pH\ 7.4} - COHb_{pH\ 7.8}$

Note that curve 1 was multiplied by 0.01 before being plot in this figure.

Figure 3:
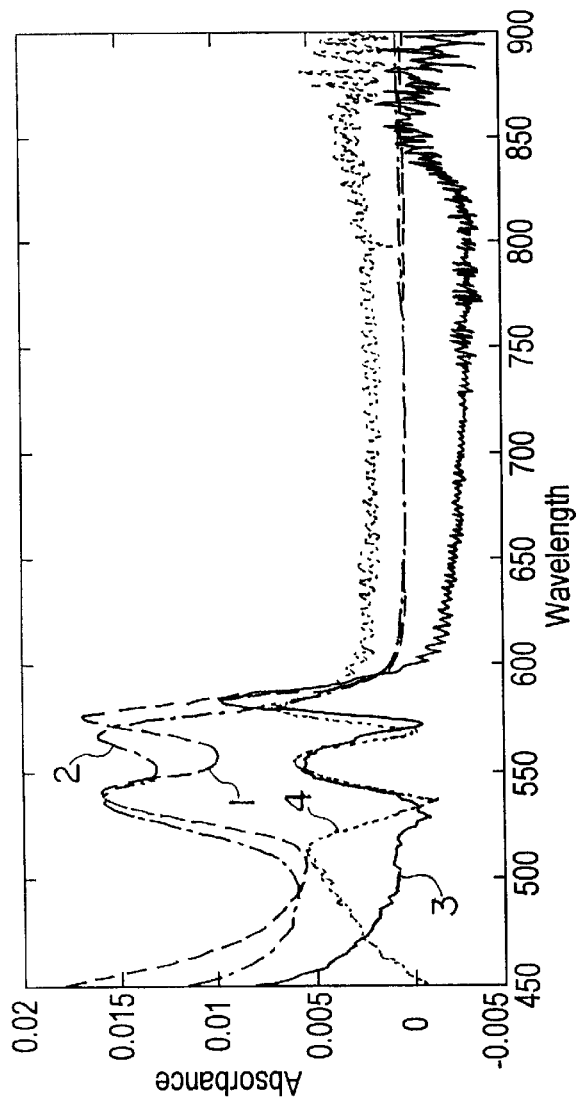

FIG. 3 is a plot of absorbance versus wavelength for:

Curve 1: $O_2Hb_{pH\ 7.2}$

Curve 2: $COHb_{pH\ 7.2}$

Curve 3: $O_2Hb_{pH\ 7.2} - O_2Hb_{pH\ 7.8}$

Curve 4: $COHb_{pH\ 7.2} - COHb_{pH\ 7.8}$

Note that curves 1 and 2 were multiplied by 0.01 before being plot in this figure.

Figure 4B:
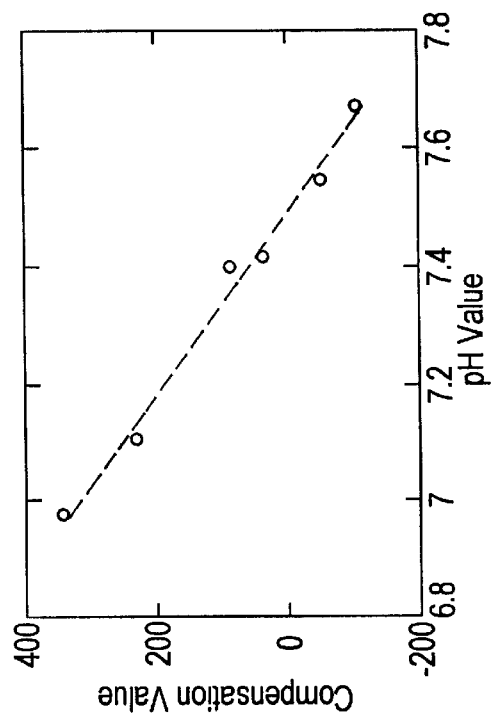
Figure 4A:
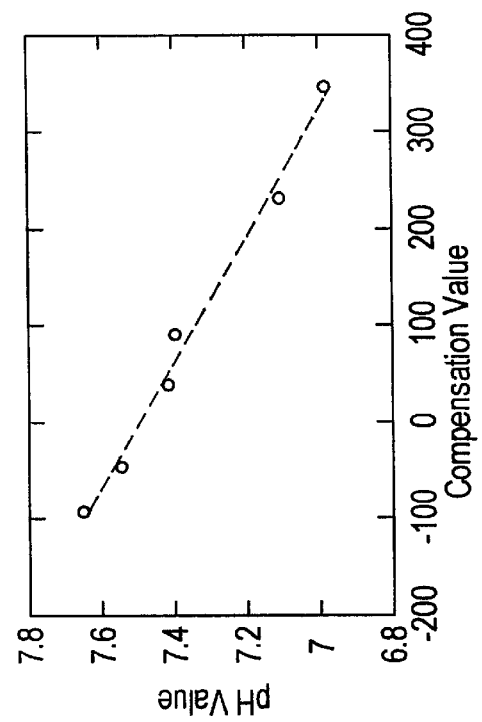

FIGS. 4A and 4B are plots of pH vs. compensation value (V) and compensation value (V) vs. pH, respectively.

The foregoing drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

DESCRIPTION OF THE PREFERRED EMBODIMENTS

As discussed above, the present invention uses the spectral changes with pH of the various fractions of hemoglobin to non-invasively determine blood pH. The preferred hemoglobin fraction is oxyhemoglobin, although carboxyhemoglobin, deoxyhemoglobin, and methemoglobin may be useful in some situations.

Oxyhemoglobin is preferred because, among other things, it is the dominant fraction of hemoglobin in normal arterial blood. Measurements on the increased blood volume in arteries and capillaries during systole provides an excellent means for non-invasively determining arterial blood values.

Absorbances measured non-invasively are affected by scattering and absorbance from other absorbers besides those contained in the patient's blood. The difference between measurements made at systole and diastole (either transmittance or reflectance) provide an effective way to measure the changes in absorbance due to arterial blood per se. Preferably, these differences are averaged over multiple measurements to reduce errors.

The blood itself includes scatters which affect the absorbance data. Preferably, the data is corrected for these effects. Various techniques are known in the art for performing such a correction. See, for example, A. Owen, "Quantitative UV-Visible Analysis in the Presence of Scattering," *Hewlett-Packard Application Note*, publication 12-5963-3937E, 1995, pages 0–7.

The preferred spectral region for evaluating the spectral factors of the invention is between about 520 nm and about 680 nm. Although a transmission measurement is the preferred method for obtaining a spectrum, a reflectance measurement is more practical for non-invasive applications when the measurement region of interest has high absorbance.

Figure 1A:
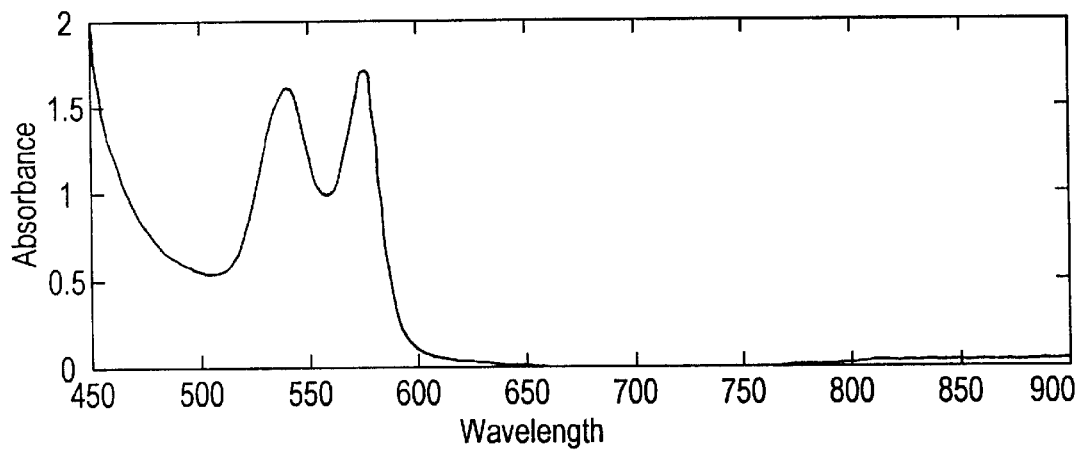
FIG. 1A is a plot of absorbance versus wavelength for $O_2Hb_{pH\ 7.2}$.
Figure 1B:
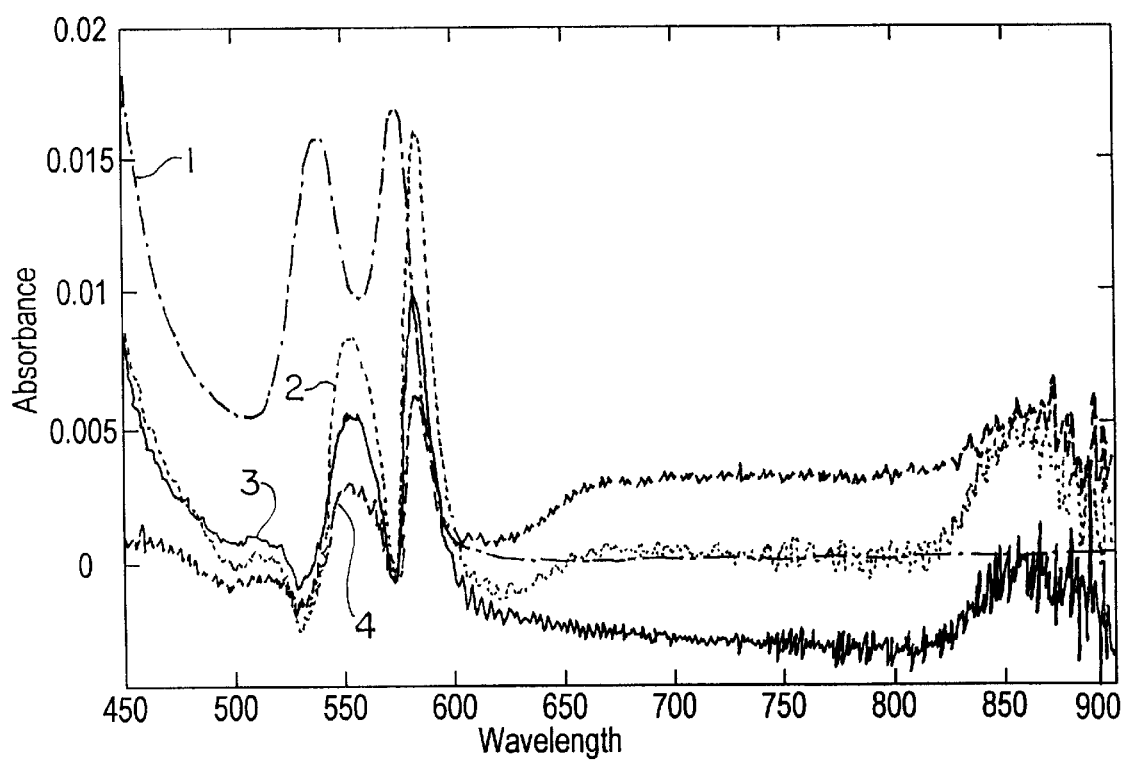

FIGS. 1 and 2 show the effects of pH on the spectra of $O_2Hb$ and COHb, respectively. FIG. 1A shows the spectrum of $O_2Hb$ at pH 7.2. For the absorbance scale used in this figure, the spectra for pH 7.5 and pH 7.8 are visually identical to that shown for pH 7.2. FIG. 1B shows the differences between the spectra at pH 7.2 and pH 7.8 (curve 2), pH 7.2 and pH 7.5 (curve 3) and pH 7.5 and pH 7.8 (curve 4). Similar curves for COHb are shown in FIGS. 2A and 2B, the only difference being that the central pH for FIG. 2B is 7.4, rather than 7.5 as in FIG. 1B. FIG. 3 shows selected curves from FIGS. 1 and 2, namely the spectrum of $O_2Hb$ at pH 7.2 (curve 1), the spectrum of COHb at pH 7.2 (curve 2), the differences between the spectra at pH 7.2 and pH 7.8 for $O_2Hb$ (curve 3), and the differences between the spectra at pH 7.2 and pH 7.8 for COHb (curve 4).

Although spectral changes are evident over much of the measurement range from 450 nm to 900 nm, the changes in the spectral region between about 520 nm and about 680 nm, specifically, between 530 nm and 650 nm, are more readily distinguished. The offsets observed in the spectral region from 650 nm to 800 nm are also substantial and may be useful, but can be confused with other effects from temperature and scatter.

The data of FIGS. 1B and 2B can be used to generate a component vector (spectral factor) which represents pH. A classical least squares (CLS) or other multivariate technique (e.g., PCR or PLS) can be used to perform the analysis.

The approach in the case of CLS is as follows, where only a component vector for oxyhemoglobin is considered initially to simplify the presentation. The use of a single vector has the disadvantage that pH effects from other hemoglobin fractions are not included. These effects may be important if oxyhemoglobin is not the dominant fraction. Spectral factors representing the pH effects of other fractions, can be included, and a procedure for doing so is discussed below. In the limit, all of the hemoglobin fractions can be used if desired.

The notation used herein for the CLS analysis, assuming "n" hemoglobin fractions (e.g., $O_2Hb$, MetHb, COHb, and HHb for n=4), is as follows:

A absorbance vector representing measured absorbances at specified intervals over a specified range of wavelengths (e.g., a 161 element column vector for absorbance measurements in 1 nm intervals over the range from 520 nm to 680 nm (the "data set"));

E extinction matrix representing the extinction coefficients for the n fractions (e.g., a n column by 161 row matrix for the above data set); if desired, the extinction matrix can have an additional column to account for scatter;

C concentration vector representing the estimated concentrations of the n fractions (i.e., a n element column vector);

P pH vector comprising the difference in absorbance of oxyhemoglobin at two different pH levels (e.g., a 161 element column vector for the above data set);

V the magnitude of the pH effect;

EP expanded extinction matrix which includes the extinction coefficients and the pH vector as an additional column (EP=augment(E,P));

CV expanded concentration vector which includes the estimated concentrations and the pH effect (CV=stack (C,V)).

In terms of these variables, the basic model can be written:

$$A = E \cdot C + P \cdot V \qquad \text{(Eq. 1)}$$

or in terms of EP and CV:

$$A = EP \cdot CV \quad \text{(Eq. 2)}$$

Letting $EP_{inv}$ represent the transformation matrix for the least squares calculation, we can write:

$$EP_{inv} = (EP^T \cdot EP)^{-1} \cdot EP^T \quad \text{(Eq. 3)}$$

so that the direct (least squares) solution for estimating concentrations and the pH effect becomes:

$$CV = EP_{inv} \cdot A \quad \text{(Eq. 4)}$$

The value of V obtained from equation 4 can be transformed into a pH value by means of the following equation, where $K_0$ and $K_1$ are calibration constants and $C_{O2Hb}$ is the concentration of oxyhemoglobin obtained from the C vector:

$$pH = K_0 + K_1 (V/C_{O2Hb}) \quad \text{(Eq. 5)}$$

One method for including pH vectors for all hemoglobin fractions is to first estimate the concentrations for the fractions and then determine the magnitude of the pH effect. In accordance with this method, a first estimate is obtained for the concentrations of the hemoglobin fractions in accordance with the following equation:

$$C_{est} = E_{inv} \cdot A \quad \text{(Eq. 6)}$$

where $E_{inv}$ is given by:

$$E_{inv} = (E^T \cdot E)^{-1} \cdot E^T \quad \text{(Eq. 7)}$$

An estimate for a combined pH vector ($P_{est}$) representing the effects of all of the hemoglobin fractions is then obtained by multiplying $C_{est}$ by a matrix (MP) composed of "n" pH vectors, each vector comprising the difference in absorbance of a hemoglobin fraction at two different pH levels, where "n" is again the number of fractions:

$$P_{est} = MP \cdot C_{est} \quad \text{(Eq. 8)}$$

$P_{est}$ is then substituted for P in equations 1 to 4 above and used to obtain an improved estimate of the concentrations of the fractions and a value for V. The improved concentration estimates can be used to further improve $P_{est}$, and the calculation repeated. Further iterations can be performed if desired.

Alternatively, instead of using equations 6 and 7, an a priori estimate for the concentrations $C_{est}$ can be made thus allowing a $P_{est}$ to be used in the initial evaluation of equations 1 to 4. With arterial blood, oxyhemoglobin is typically the overwhelming major component, so a good $P_{est}$ is obtaining simply by using the oxyhemoglobin vector, as was done in the original derivation of equations 1 to 4 set forth above.

By means alternations 1 through 4, or alternatively, 1 through 8, an absorption spectrum of a patient's arterial blood, obtained non-invasively, can be used to determine the pH of the blood.

Without intending to limit it in any manner, the present invention will be more fully described by the following examples.

EXAMPLE 1

E Matrix

An E matrix for wavelength steps of 1 nm over the wavelength range from 520–680 nm was obtained using: (1) samples of lysed blood adjusted to contain essentially only a single hemoglobin fraction, and (2) a reference spectrometer sold under the trademark CARY 4 by Varian Associates, Palo Alto, Calif.

The reference spectrophotometer produced an absorbance value every nanometer with a 0.5 nanometer spectral bandwidth. A bandwidth correction was performed to obtain E matrix values appropriate to the Ciba Corning 800 Series CO-ox instrument on which experimental measurements were made (see below). The bandwidth correction was made by convolving the spectra obtained on the Cary with the measured spectral response of the 800 Series CO-ox, which is approximately 2 nanometers.

A correction was also performed to the E matrix to take account of the fact that lysed blood was used in the construction of the matrix, while the matrix was to be used with unlysed blood. That correction involved adjusting the oxyhemoglobin spectrum in the manner described in the above-referenced article by Wimberley et al. so as to achieve hemoglobin fractions which generally agreed with those measured using a reference instrument. In particular, the correction involved using reference values for hemoglobin concentrations and adjusting the E matrix based on the differences in calculated spectra versus measured spectra. An additional column vector was also included in the E matrix to account for scatter.

The elements of that vector were given by $(600/\text{wavelength})^{0.5}$, where the wavelengths were in nanometers The E matrix was tested using unlysed blood from a single donor which was tonometered with six different gas mixtures selected to vary pH via $pCO_2$. Five samples were obtained for each of the six experimental conditions (total samples=30), and an absorption spectrum (A vector) was generated for each of the samples using a 800 Series CO-ox manufactured by Ciba Corning Diagnostics Corp., Medfield, Mass.

Each spectrum was analyzed using equations 6 and 7 above to generate concentration values for $O_2Hb$, MetHb, COHb, and HHb, and the five values for each experimental condition were averaged. The results are shown in Table 1, where total hemoglobin (tHb) is reported in gm/dl and the fractions are reported in percent of the total. The small standard deviations shown in the table demonstrate that the E matrix is effective in determining concentrations.

As a reference, samples were analyzed using an OSM-3 Spectrometer manufactured by Radiometer A/S, Copenhagen, Denmark. The results of these tests are shown in Table 2 and the differences between the measurements of Tables 1 and 2 are shown in Table 3. As can be seen in Table 3, the E matrix analysis produced similar, although not identical, concentration values to the reference system.

EXAMPLE 2

Determination of pH pH values for the thirty samples were measured electrochemically using two different instruments and averaged. The pH's varied from about 7.0 to about 7.6.

V values were obtained using: (1) equation 4 and the E matrix of Example 1; (2) the thirty A vectors; and (3) a P vector obtained from curve 2 of FIG. 1B. The five V values for each experimental condition were averaged.

FIG. 4 plots the average V values (compensation values) versus pH. As clearly shown in this figure, the V values are excellent predictors of pH.

pH values were obtained from the V values using equation 5 above, with $K_0 = 7.478$ and $K_1 = -0.00161$. These values were compared to the pH values measured electrochemically. The standard error between the two techniques was 0.026 pH units. A second order least squares fit reduced the standard error to 0.025 pH units. That fit involved a second order or quadratic approximation to the relationship between V and measured pH.

For reference, the pH measurements obtained electrochemically using the two different instruments differed by an average of 0.012 pH units. The standard error of prediction of pH using the invention is thus consistent with the measurement variability. A better correlation can be expected through the use of additional samples.

The data of this example clearly demonstrates that pH can be accurately determined using multivariate analysis and a spectral factor based on the difference in the absorbance spectra of a hemoglobin fraction at two pH's.

The mathematical operations described herein can be performed using a variety of computers and software. For example, those operations can be performed using the commercially available MATHCAD program (MathSoft, Inc., Cambridge, Mass.) and a personal computer configured to run that program in accordance with the program manufacturer's specifications.

Although preferred and other embodiments of the invention have been described herein, further embodiments may be perceived by those skilled in the art without departing from the scope of the invention as defined by the following claims.

performing multivariate analysis on the absorption spectrum so obtained, wherein the multivariate analysis incorporates a first spectral factor, said first spectral factor comprising a vector based on the change in the spectrum of a first hemoglobin fraction as measured at a minimum of two different pH's of said first hemoglobin fraction and a magnitude of the pH effect.

2. The method of claim 1 wherein the first hemoglobin fraction is oxyhemoglobin.

3. The method of claim 1 wherein two different pH's of said first hemoglobin fraction include pH's of about 7.2 and about 7.8.

4. The method of claim 1 wherein at least one additional spectral factor is incorporated in the analysis, said at least one additional spectral factor comprising a vector based on the change in the spectrum of at least one additional hemoglobin fraction as measured at a minimum of two different pH's of said at least one additional hemoglobin fraction and a magnitude of the pH effect, said at least one additional hemoglobin fraction being different from the first hemoglobin fraction.

5. The method of claim 1 wherein the multivariate analysis is a classical least squares analysis.

6. The method of claim 1 wherein at least some of the plurality of wavelengths lie between about 520 nm and about 680 nm.

7. The method of claim 1 wherein the blood pH is determined non-invasively.

|  | 1 | | 2 | | 3 | | 4 | | 5 | | 6 | |
|---|---|---|---|---|---|---|---|---|---|---|---|---|
|  | Mean | Std Dev | Mean | Std Dev | Mean | Std Dev | Mean | Std Dev | Mean | Std Dev | Mean | Std Dev |
| Table 1 Experimental | | | | | | | | | | | | |
| tHb | 14.4 | 0.04 | 14.5 | 0.15 | 14.5 | 0.11 | 14.5 | 0.06 | 14.8 | 0.08 | 14.6 | 0.12 |
| HHb | 0.1 | 0.06 | 0.1 | 0.06 | 0.2 | 0.05 | 3.2 | 0.05 | 1.6 | 0.05 | 5.9 | 0.08 |
| $O_2Hb$ | 99.2 | 0.07 | 100.1 | 0.22 | 99.2 | 0.37 | 95.8 | 0.10 | 96.2 | 0.13 | 92.2 | 0.20 |
| COHb | 0.3 | 0.06 | 0.2 | 0.08 | 0.5 | 0.14 | 0.5 | 0.05 | 0.7 | 0.07 | 0.5 | 0.08 |
| MetHb | 0.4 | 0.08 | −0.4 | 0.19 | 0.1 | 0.27 | 0.5 | 0.10 | 1.5 | 0.11 | 1.3 | 0.11 |
| Table 2 Reference | | | | | | | | | | | | |
| tHb | 14.5 | 0.04 | 14.5 | 0.14 | 14.5 | 0.12 | 14.5 | 0.12 | 14.7 | 0.16 | 14.5 | 0.08 |
| HHb | 0.5 | 0.09 | 0.4 | 0.10 | 0.4 | 0.10 | 3.4 | 0.16 | 2.5 | 0.10 | 6.5 | 0.13 |
| $O_2Hb$ | 99.4 | 0.04 | 99.3 | 0.12 | 99.3 | 0.12 | 96.2 | 0.15 | 97.4 | 0.15 | 93.4 | 0.80 |
| COHb | −0.4 | 0.05 | −0.2 | 0.09 | −0.2 | 0.09 | −0.2 | 0.05 | −0.4 | 0.11 | −0.5 | 0.08 |
| MetHb | 0.6 | 0.05 | 0.5 | 0.10 | 0.5 | 0.10 | 0.6 | 0.05 | 0.6 | 0.11 | 0.6 | 0.08 |
| Table 3 Experimental/Reference Difference | | | | | | | | | | | | |
| tHb | −0.1 | 0.00 | 0.0 | 0.01 | 0.0 | −0.01 | 0.0 | −0.06 | 0.1 | −0.08 | 0.1 | 0.04 |
| HHb | −0.4 | −0.03 | −0.3 | −0.05 | −0.2 | −0.06 | −0.2 | −0.11 | −0.9 | −0.05 | −.6 | −0.05 |
| $O_2Hb$ | −0.2 | 0.03 | 0.8 | 0.10 | −0.1 | 0.25 | −0.4 | −0.05 | −1.2 | −0.02 | −1.2 | −0.60 |
| COHb | 0.7 | 0.01 | 0.4 | −0.01 | 0.7 | 0.05 | 0.7 | 0.00 | 1.1 | −0.04 | 1.0 | 0.00 |
| MetHb | −0.2 | 0.03 | −0.9 | 0.09 | −0.4 | 0.17 | −0.1 | 0.05 | 0.9 | 0.00 | 0.7 | 0.03 |

What is claimed is:

1. A method for determining blood pH comprising the steps of:
   measuring the absorption of the blood at a plurality of wavelengths; and 8. The method of claim 7 wherein the absorption of the blood is determined by measuring the absorption of blood, capillaries, and tissue at systole and diastole.

* * * * *